(12) United States Patent
Barker et al.

(10) Patent No.: US 11,730,508 B2
(45) Date of Patent: Aug. 22, 2023

(54) SYSTEMS AND METHODS FOR SEPARATING TISSUE IN CORNEAL TRANSPLANT PROCEDURES

(71) Applicant: CorneaGen Inc., Seattle, WA (US)

(72) Inventors: Jerry W. Barker, Gretna, VA (US); Douglas C. Drabble, Winston-Salem, NC (US); Yousuf Khalifa, Smyrna, GA (US)

(73) Assignee: CORNEAGEN INC., Seattle, WA (US)

(*) Notice: Subject to any disclaimer, the term of this patent is extended or adjusted under 35 U.S.C. 154(b) by 433 days.

(21) Appl. No.: 17/111,490

(22) Filed: Dec. 3, 2020

(65) Prior Publication Data

US 2021/0085357 A1 Mar. 25, 2021

Related U.S. Application Data

(62) Division of application No. 16/009,501, filed on Jun. 15, 2018, now Pat. No. 10,864,013.

(Continued)

(51) Int. Cl.
*A61B 17/3203* (2006.01)
*A61F 9/007* (2006.01)
(Continued)

(52) U.S. Cl.
CPC .......... *A61B 17/3203* (2013.01); *A61F 2/142* (2013.01); *A61F 9/007* (2013.01);
(Continued)

(58) Field of Classification Search
CPC . A61B 17/3203; A61B 17/0231; A61F 9/013; A61F 9/007; A61F 9/0133; A61F 2/14; A61F 2/142
See application file for complete search history.

(56) References Cited

U.S. PATENT DOCUMENTS

| 4,903,695 | A | | 2/1990 | Warner | |
|---|---|---|---|---|---|
| 5,139,518 | A | * | 8/1992 | White | A61F 2/142 606/166 |

(Continued)

FOREIGN PATENT DOCUMENTS

| DE | 10015565 A1 | 3/2000 |
|---|---|---|
| WO | 2001005341 A1 | 1/2001 |

OTHER PUBLICATIONS

International Search Report dated Sep. 10, 2018 for PCT/US2018/037719 filed Jun. 15, 2018 (Applicant—Sightlife Surgical // Inventors—Barker et al.) (2 pages).

(Continued)

*Primary Examiner* — Vi X Nguyen
(74) *Attorney, Agent, or Firm* — Polsinelli PC

(57) ABSTRACT

A device for separating tissue in an eye includes a body configured to be positioned on the eye surface. The body receives air from one or more air supplies. The body includes one or more air supply channels. The separation device includes a plurality of needles extending from the body. Each needle includes a proximal opening, a distal opening, and a passageway extending between the proximal and distal openings. The proximal openings of the needles are coupled to the one or more air supply channels. The distal openings of the needles are spaced from the body to be positioned in eye tissue. The one or more air supply channels direct the air from the one or more air supplies into the proximal openings, through the passageways, and out the distal openings of the needles and into the eye tissue. The air applies a pressure to separate the eye tissue.

20 Claims, 4 Drawing Sheets

Related U.S. Application Data

(60) Provisional application No. 62/520,333, filed on Jun. 15, 2017.

(51) Int. Cl.
*A61F 2/14* (2006.01)
*A61B 17/30* (2006.01)

(52) U.S. Cl.
CPC .............. *A61B 2017/306* (2013.01); *A61B 2017/32035* (2013.01)

(56) References Cited

U.S. PATENT DOCUMENTS

| | | |
|---|---|---|
| 5,249,121 A | 9/1993 | Baum |
| 5,312,330 A | 5/1994 | Klopotek |
| 6,596,000 B2* | 7/2003 | Chan .............. A61M 1/774 606/205 |
| 7,364,575 B2 | 4/2008 | Van Saarloos |
| 2008/0269771 A1 | 10/2008 | Fulcher |
| 2010/0185222 A1 | 7/2010 | Keller |
| 2015/0238307 A1 | 8/2015 | Galperin |
| 2016/0106916 A1* | 4/2016 | Burmaster .......... A61M 5/1413 604/28 |

OTHER PUBLICATIONS

**International Preliminary Report on Patentability dated Dec. 17, 2019 for PCT/US2018/037719 filed Jun. 15, 2018 (Applicant—Sightlife Surgical // Inventors—Barker et al.) (5 pages).
** Written Opinion dated Sep. 10, 2018 for PCT/US2018/037719 filed Jun. 15, 2018 (Applicant—Sightlife Surgical // Inventors—Barker et al.) (4 pages).

* cited by examiner

SYSTEMS AND METHODS FOR SEPARATING TISSUE IN CORNEAL TRANSPLANT PROCEDURES

CROSS-REFERENCE TO RELATED APPLICATIONS

This application is a division of U.S. patent application Ser. No. 16/009,501, filed Jun. 15, 2018, which claims the benefit of, and priority to, U.S. Provisional Patent Application No. 62/520,333, filed Jun. 15, 2017, the contents of each of which are incorporated entirely herein by reference.

BACKGROUND

Field

The present disclosure pertains to systems and methods for transplanting a cornea to treat disorders of the eye, and more particularly, to systems and methods for separating tissue in corneal transplant procedures.

Description of Related Art

Various disorders of the eye may result from diseased/damaged corneal tissue. The diseased/damaged corneal tissue can affect vision by scattering and/or distorting light and causing glare and/or blurred vision. In some cases, proper vision can only be restored by a corneal transplant which replaces the diseased/damaged corneal tissue with healthy tissue from an organ donor.

SUMMARY

Aspects of the present disclosure provide systems and methods for separating tissue to remove diseased/damaged tissue from a recipient cornea in corneal transplant procedures. For instance, such systems and methods may separate stromal tissue from Descemet's membrane for deep anterior lamellar keratoplasty (DALK).

According to one embodiment, a system for separating tissue in an eye includes a separation device. The separation device includes a body configured to be positioned on a surface of an eye. The body is configured to receive air from one or more air supplies. The body including one or more air supply channels. The separation device includes a plurality of needles extending from the body. Each needle includes a proximal opening, a distal opening, and a passageway extending between the proximal opening and the distal opening. The proximal openings of the needles are coupled to the one or more air supply channels of the body. The distal openings of the needles are spaced from the body to be positioned in tissue of the eye when the body is positioned on the surface of the eye. The one or more air supply channels are configured to direct the air from the one or more air supplies into the proximal openings, through the passageways, and out the distal openings of the needles and into the tissue of the eye. The air applies a pressure to separate the tissue of the eye. In some embodiments, the distal openings of the needles are spaced from the body such that when the body is positioned on the surface of the eye, the distal openings are positioned between a stroma and Descemet's membrane of a cornea of the eye.

According to another embodiment, a method for separating tissue in an eye includes positioning a body of a separation device on a surface of an eye such that a plurality of needles extending from the body move into tissue of the eye. The method includes coupling the body to one or more air supplies. The method includes operating the one or more air supplies to deliver air to one or more air supply channels of the body. Each needle includes a proximal opening, a distal opening, and a passageway extending between the proximal opening and the distal opening. The proximal openings of the needles are coupled to the one or more air supply channels of the body. The distal openings of the needles spaced from the body and positioned in the tissue of the eye. The one or more air supply channels direct the air from the one or more air supplies into the proximal openings, through the passageways, and out the distal openings of the needles and into the tissue of the eye. The air applies a pressure to separate the tissue of the eye. Positioning the body of the separation device on the surface of the eye may cause the distal openings of the needles to be positioned between a stroma and Descemet's membrane of a cornea of the eye to separate the stroma from the Descemet's membrane.

DETAILED DESCRIPTION

Various disorders of the eye may result from diseased/damaged corneal tissue. The diseased/damaged corneal tissue can affect vision by scattering and/or distorting light and causing glare and/or blurred vision. In some cases, proper vision can only be restored by a corneal transplant which replaces the diseased/damaged corneal tissue with healthy tissue from an organ donor.

From the outer (anterior) surface of the eye to the inner (posterior) parts, the structure of the cornea includes five layers: (1) epithelium (approximately 50 µm thick), (2) Bowman's layer (approximately 20 µm thick), (3) stroma (approximately 500 µm thick), (4) Descemet's membrane (approximately 10 µm thick), and (5) endothelium (approximately 5 µm thick). Penetrating keratoplasty (PK) involves a full-thickness transplant where all layers of a cornea from the epithelium to the endothelium are removed and replaced with a corneal implant. In PK, a manual dissection device known as a trephine may be employed to remove the full thickness of existing corneal tissue. The trephine may also be used to cut a donor cornea to provide the corneal implant that dimensionally matches the removed corneal tissue. The corneal implant is then positioned in place of the removed corneal tissue and sutured into place.

Deep anterior lamellar keratoplasty (DALK) is an alternative treatment that selectively replaces diseased/damaged tissue in an anterior portion of a recipient cornea. In particular, DLAK removes an anterior portion including the epithelium, Bowman's layer, and the stroma, but leaves a posterior portion including the native Descemet's membrane and endothelium in place. A dimensionally matching corneal implant from a donor cornea is then positioned in a bed formed by the removal of the anterior portion in the recipient cornea and sutured into place.

DALK is less invasive than PK and is preferred when the endothelium is healthy. In contrast to the cells of the epithelium and the stroma, the cells of the endothelium cannot regenerate. With DALK, patients retain their own endothelium so the risk of rejection by the immune system may be dramatically reduced.

Figure 1:
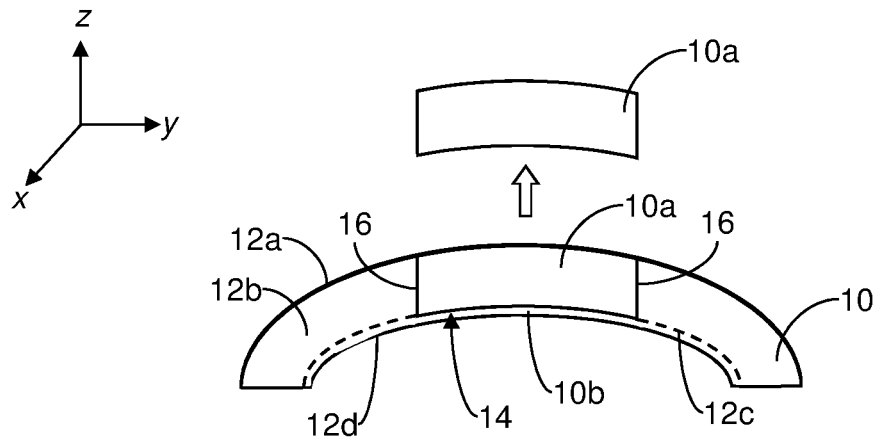
FIG. 1 illustrates an example corneal transplant procedure where stromal tissue is separated from Descemet's membrane to remove tissue from a recipient cornea, according to aspects of the present disclosure.

FIG. 1 illustrates a recipient cornea 10 including epithelium 12a, stroma 12b, Descemet's membrane 12c, and endothelium 12d. According to aspects of the present disclosure, embodiments apply air between the stroma 12b and Descemet's membrane 12c. The air applies sufficient pressure to cause a separation 14 between the stroma 12b and the Descemet's membrane 12c. After the separation 14 is created, a cutting device can be applied to the recipient cornea 10 to make a cut 16 that extends from the epithelium 12a to the separation 14. For instance, the cutting device may be a trephine with a blade that makes a substantially circular cut at each depth (parallel to the x-y plane shown in FIG. 1) from the epithelium 12a to the separation 14. The separation 14 and the cut 16 define an anterior portion 10a of corneal tissue that is removed from the recipient cornea 10. After removal of the anterior portion 10a, a posterior portion 10b (including the Descemet's membrane 12c and the endothelium 12d) is left in place to define a bed for receiving a corneal implant for DALK.

Figure 2:
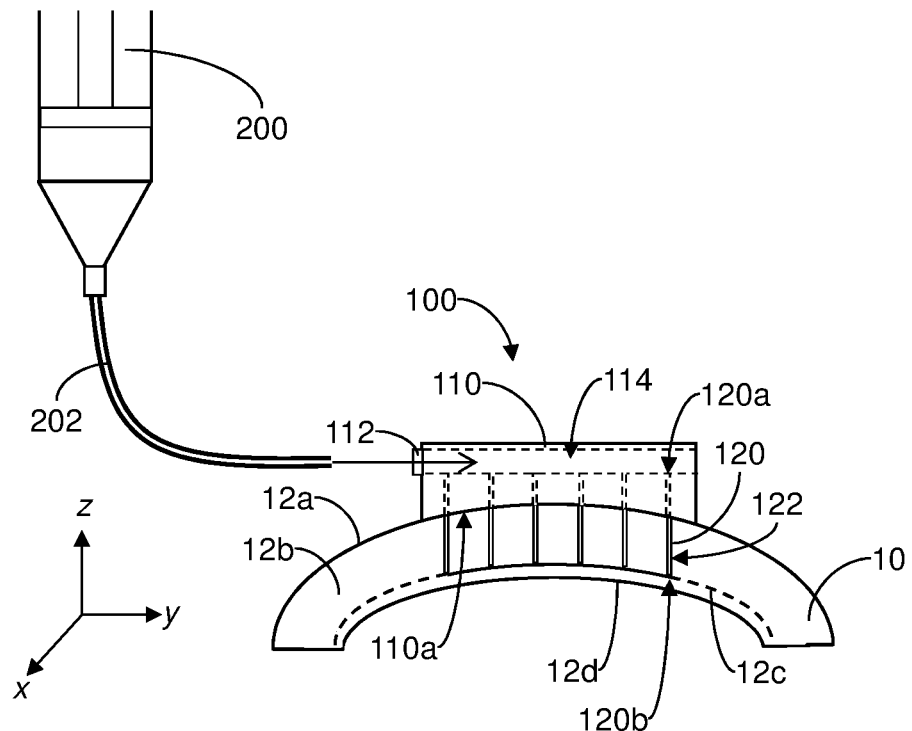
FIG. 2 illustrates an example separation device including a plurality of needles that apply air from an air supply between the stroma and Descemet's membrane to cause a separation therebetween, according to aspects of the present disclosure.

FIG. 2 illustrates an example separation device 100 for separating the stroma 12b and the Descemet's membrane 12c to remove tissue from the recipient cornea 10. The separation device 100 includes a body 110 and a plurality of needles (or micro-needles) 120 that extend from the body 110. The needles 120 may be formed from stainless steel with the appropriate gauge and the body 110 may be formed from stainless steel or a plastic.

The body 110 can be positioned on the outer surface of the recipient cornea 10, i.e., the epithelium 12a. In particular, the separation device 100 is lowered in the negative z-direction as shown in FIG. 2 to position the body 110 on the epithelium 12a. The body 110 may include a contact surface 110a that is contoured to accommodate the shape of the epithelium 12a.

As the separation device 100 is lowered onto the epithelium 12a, the needles 120 penetrate the recipient cornea 10, passing through the epithelium 12a, Bowman's layer (not shown), and the stroma 12b. Each needle 120 includes a passageway 122 that extends from a proximal opening 120a to a distal opening 120b. The proximal opening 120a of each needle 120 is positioned at or in the body 110. Meanwhile, the distal opening 120b of each needle 120 is positioned at a distance from the body 110. When the body 110 is positioned on the epithelium 12a, the distal opening 120b is positioned approximately between the stroma 12b and the Descemet's membrane 12c. For instance, the needles 120 may extend to a depth of approximately 570 μm in the recipient cornea 10 to position the distal openings 120b between the stroma 12b and the Descemet's membrane 12c. Various separation devices with varying dimensions, e.g., different needle lengths, may be provided to accommodate specific patient needs and characteristics, e.g., different thicknesses for corneal layers.

The body 110 includes a port 112 that can be coupled to an air supply 200 via a connecting tube 202. The body 110 includes one or more air supply channels 114 that connect the port 112 to the proximal openings 120a of the needles 120. The air supply 200 can be operated to deliver a predetermined amount of air through the proximal openings 120a. For instance, the air supply 200 may be a syringe with a plunger than can be operated to push air into the connecting tube 202 and through the port 112 and the air supply channels 114.

The air delivered from the air supply 200 travels through the needles 120, i.e., into the proximal openings 120a, through the passageways 122, and out the distal openings 120b. When the body 110 is positioned on the epithelium 12a, the air exits the distal openings 120b into areas between the stroma 12b and the Descemet's membrane 12c. The distal openings 120b are positioned at various respective locations between the stroma 12b and the Descemet's membrane 12c. Specifically, the body 110 is positioned on the epithelium 12a so that the needles 120 deliver the air from the air supply 200 to desired locations. The air creates sufficient pressure at the desired locations to separate the stroma 12b from the Descemet's membrane 12c. Advantageously, the use of the plurality of needles 120 distributes air pressure across the desired locations for more efficient and precise separation of the stroma 12b from the Descemet's membrane 12c.

As described above, after the stroma 12b is separated from the Descemet's membrane 12c, a cutting device, e.g., a trephine, can be applied to the recipient cornea 10 to make a cut that extends from the epithelium 12a to the separation. As such, the anterior portion 10a of the recipient cornea 10 can be removed to allow for a corneal implant.

Aspects of the separation device 100, e.g., the air supply channels 114 of the body 110 and/or the needles 120, may be configured to deliver the air with substantially similar airflow at each distal opening 120b. Alternatively, aspects of the separation device 100 may be configured to deliver the air with varying airflows via different respective needles 120 for more effective separation at particular areas between the stroma 12b and the Descemet's membrane 12c. For instance, a first needle may have a first passageway with a smaller cross-sectional area than a second passageway of a second needle, so that the airflow through the first needle has a greater velocity than the airflow through the second needle.

Figure 3A:
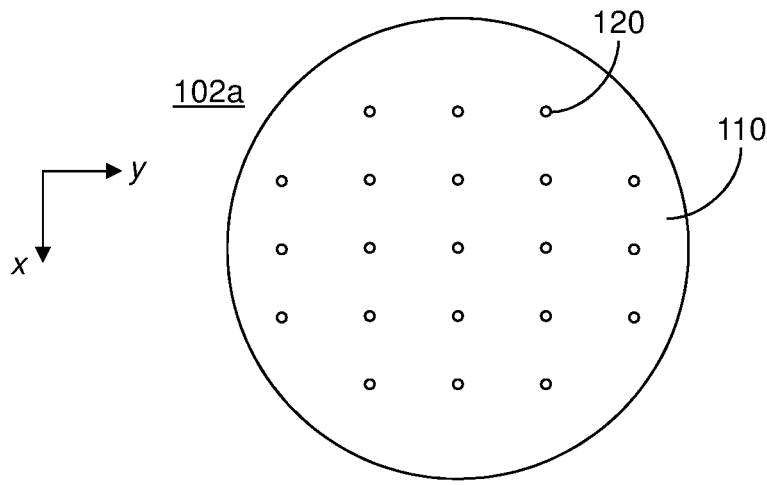
FIG. 3A illustrates an example pattern of needles that applies air from an air supply between the stroma and Descemet's membrane to cause a separation therebetween, according to aspects of the present disclosure.

FIG. 3A illustrates an example pattern 102a of needles 120 extending from the body 110 to apply air to desired locations between the stroma 12b and the Descemet's membrane 12c. In particular, the needles 120 are arranged uniformly in a grid. The number of needles 120 per area is substantially uniform across the pattern 102a (excluding the edges). As such, if each needle 120 provides substantially the same airflow, a more uniform amount of air can be delivered across the pattern 102a (excluding the edges).

Figure 3B:
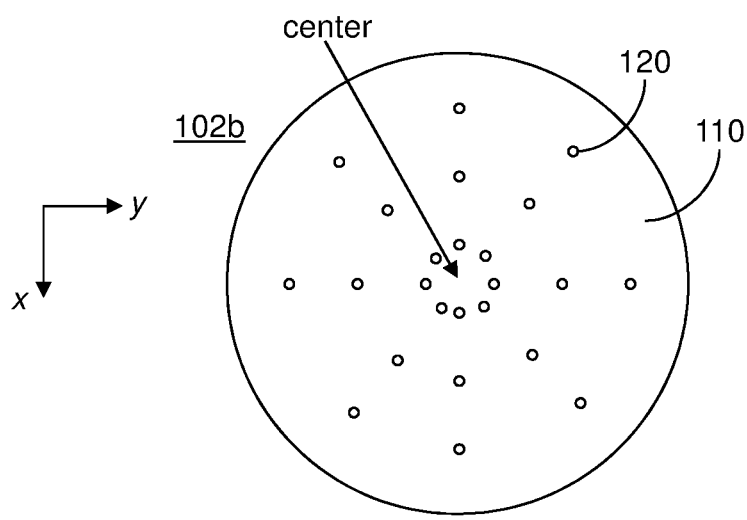
FIG. 3B illustrates another example pattern of needles that applies air from an air supply between the stroma and Descemet's membrane to cause a separation therebetween, according to aspects of the present disclosure.

Alternatively, FIG. 3B illustrates another example pattern 102b of needles 120 extending from the body 110. In particular, the needles 120 are arranged in lines that extend radially outward from a center. Approaching the center of the pattern 102b, the number of needles 120 per area increases. Thus, if each needle 120 provides substantially the same airflow, more air is delivered at the center of the pattern 102b. The pattern 102 may be employed, for instance, if more air pressure is desired at the center for more effective separation of the stroma 12b and the Descemet's membrane 12c.

Although FIGS. 3A-B illustrate specific needle patterns 102a, b, the needles 120 in other embodiments may be arranged according to other patterns. For instance, the needles 120 may be arranged to deliver air according to non-circular and/or asymmetric patterns. The needles may be arranged with non-uniform spacing between the needles across the pattern. The number of needles 120 per area may vary across the pattern in any manner to deliver more air where desired. Furthermore, in addition to being arranged according to a particular pattern, different needles 120 may deliver the air with varying respective airflows.

As described above, the body 110 of the separation device 100 is positioned on the epithelium 12a to deliver the air to desired locations via the needles 120. To keep the body 110 in a stable position on the epithelium 12a for precise operation of the separation device 100, embodiments may include a staging device that couples the body 110 to the cornea 10 and minimizes relative motion between the body 12a and the cornea 10.

Figure 4:
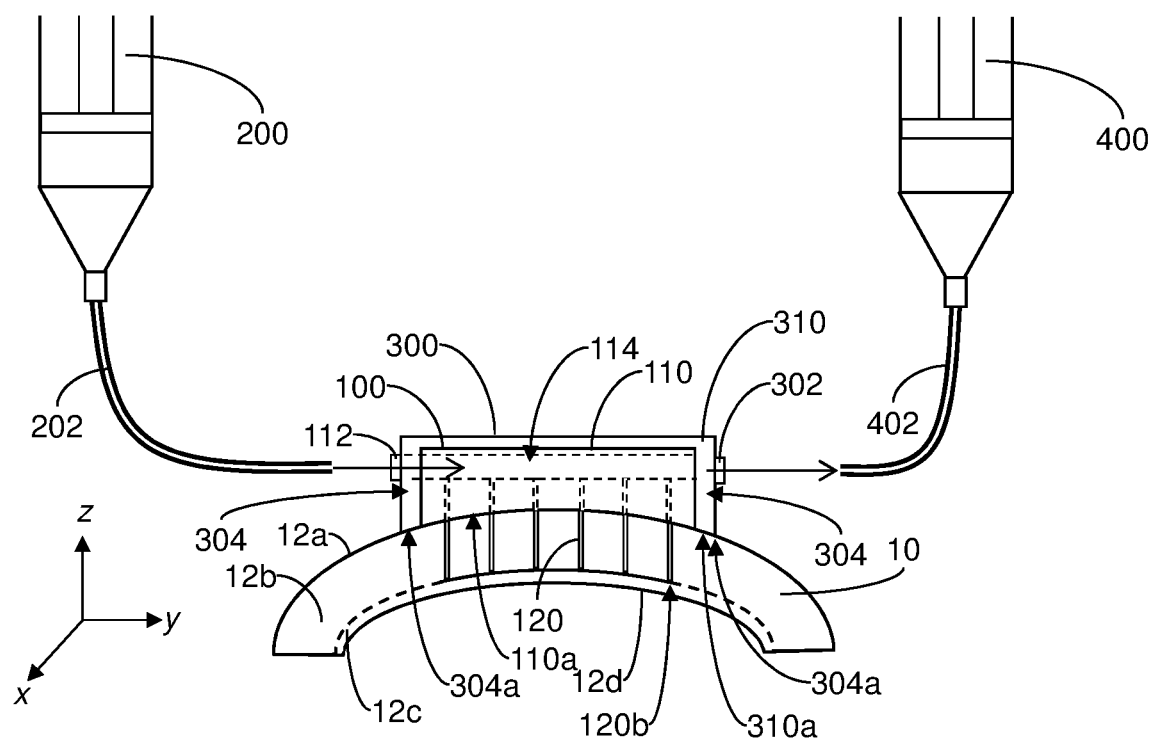
FIG. 4 illustrates the separation device of FIG. 1 stably coupled to the cornea via an example staging device, according to aspects of the present disclosure.

FIG. 4 illustrates an example staging device 300 for positioning the separation device 100. The staging device 300 includes a body 310 that holds the separation device 100. For instance, the body 310 may be a ring with a central aperture in which the body 110 of the separation device 100 can be fixedly positioned.

The body 310 also includes a contact surface 310a that is contoured to engage the epithelium 12a. Additionally, the body 310 includes a port 302 that can be coupled to a vacuum source 400 via a connecting tube 402. Furthermore, the body 310 includes one or more vacuum channels 304 that are connected to the port 302. The vacuum channels 304 include one or more openings 304a at the contact surface 310a.

The vacuum source 400 can be operated to generate negative pressure in the vacuum channels 304. For instance, the vacuum source 400 may be a syringe with a plunger than can be operated to draw air from the vacuum channels 304 via the port 302 and the connecting tube 402. The negative pressure creates suction at the one or more openings 304a, causing the contact surface 310a of the staging device 300 to engage the epithelium 12a. This engagement stably positions the staging device 300 and thus the separation device 100 on the epithelium 12a. As such, relative movement between the separation device 100 and the cornea 10 can be minimized. After the separation device 100 is operated to separate the stroma 12b from the Descemet's membrane 12c as described above, the vacuum source 400 can be operated to release the staging device 300 and the separation device 100 from the cornea 10.

Figure 5:
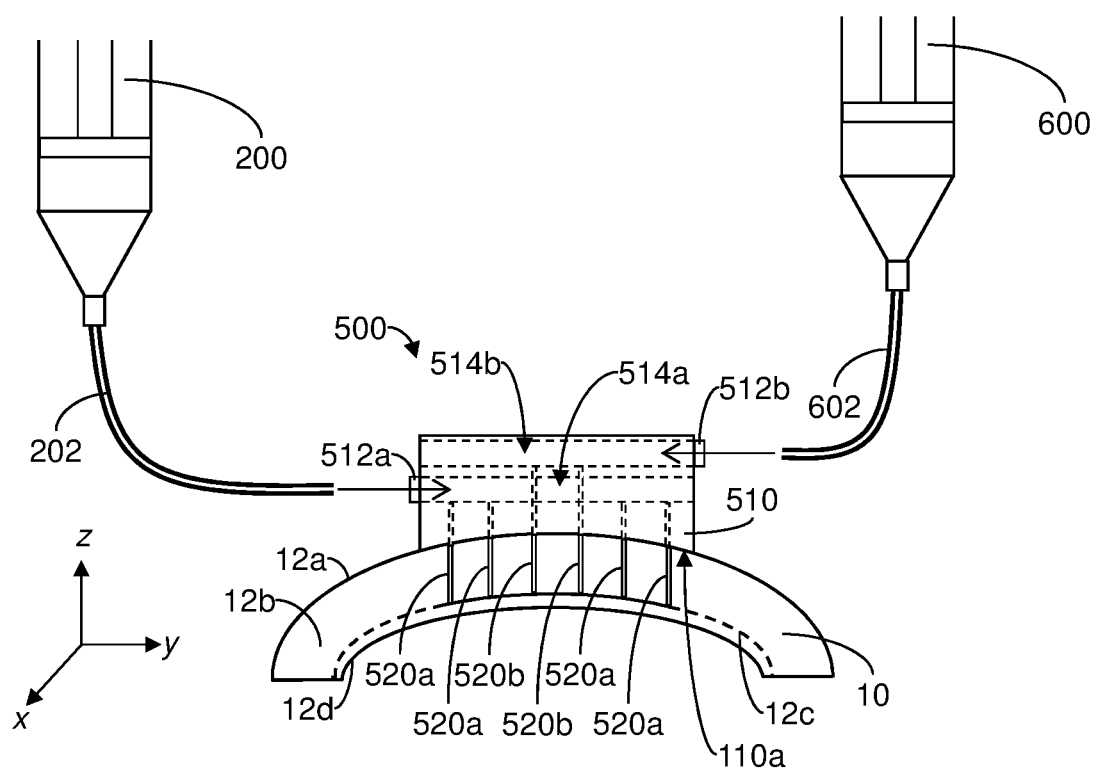
FIG. 5 illustrates another example separation device including more than one subset of needles that applies air from more than one air supply between the stroma and Descemet's membrane to cause a separation therebetween, according to aspects of the present disclosure.

As described above, the separation device 100 may be coupled to the air supply 200 to deliver air through each needle 120. Other embodiments, however, may employ more than one air supply to deliver air to the needles. For instance, FIG. 5 illustrates another example separation device 500 which is coupled to more than one air supply. The separation device 500 includes a body 510 and a plurality of needles 520a, b. Similar to the separation device 100 described above, the needles 520a, b extend to areas between the stroma 12b and the Descemet's membrane 12c when the body 510 is positioned on the epithelium 12a. Thus, the needles 520a, b can apply air to separate the stroma 12b from the Descemet's membrane 12c. Unlike the separation device 100, however, the separation device 500 includes a first port 512a that can be coupled to the first air supply 200 via the first connecting tube 202 and a second port 512b that can be coupled to a second air supply 600 via a second connecting tube 602.

As shown in FIG. 5, the separation device 500 includes a first subset of needles 520a and a second subset of needles 520b. The body 510 includes a first subset of one or more air supply channels 514a that connect the port 512a to the first subset of needles 520a. Additionally, the body 510 includes a second subset of one or more air supply channels 514b that connect the port 512b to the second subset of needles 520b.

The first subset of needles 520a and the second subset of needles 520b are separately coupled to the first air supply 200 and the second air supply 600, respectively. As such, the first air supply 200 can be operated to deliver a first amount of air to the first subset of needles 520a. Meanwhile, the second air supply 600 can be separately operated to deliver a second amount of air to the second subset of needles 520b. As described above, the first air supply 200 may be a syringe with a plunger than can be operated to push air into the connecting tube 202 and through the port 512a and the air supply channels 514a. Similarly, the second air supply 600 may also be a syringe.

Advantageously, the use of more than one air supply allows different amounts of air to be delivered to different subsets of needles, respectively. This provides control over the amounts of air delivered to different areas between the stroma 12b and the Descemet's membrane 12c. For instance, as shown in FIG. 5, the first subset of needles 520a may be positioned on the periphery of the needle pattern for the separation device 500, while the second subset of needles 520b may be positioned in the center of the needle pattern. As such, if less (or more) air is desired on the periphery of the needle pattern to separate the stroma 12b from the Descemet's membrane 12c, the first air supply 200 may be selectively operated to deliver, to the first subset of needles 520a, a lesser (or greater) amount of air than the amount of air delivered to the second subset of needles 520b with the second air supply 600.

Although the first air supply 200 and the second air supply 600 may be operated to deliver air to the needles 520a, b substantially simultaneously, it is contemplated that the first air supply 200 and the second air supply 600 may be operated at different times to separate different areas of the stroma 12b from the Descemet's membrane 12c during different temporal stages. For instance, the first air supply 200 may be operated at a first time to separate the stroma 12b from the Descemet's membrane 12c on the periphery of the needle pattern, and the second air supply 600 may be subsequently operated at a second time to separate the stroma 12b from the Descemet's membrane 12c at the center of the needle pattern.

In general, the use of more than one air supply can provide greater control over the delivery of air via different needles. Although the separation device 500 in FIG. 5 may employ two air supplies 200, 600 for two subsets of needles 520a, b, other embodiments may include more than two air supplies for more than two subsets of needles. A subset of needles may include one or more needles. It is also contemplated that a subset of needles may be coupled to more than one air supply. Moreover, although the first subset of needles 520a may be positioned on the periphery of the needle pattern and the second subset of needles 520b may be positioned at the center of the needle pattern, in other embodiments the needles in a subset connected to a particular air supply may be positioned in any location(s) in the needle pattern.

Although the air supplies and vacuum supply described above may include syringes, other embodiments may employ other devices, e.g., small pumps, to deliver air to the separation device and/or generate a negative pressure in the staging device.

Although the example embodiments described above may involve separating stromal tissue from Descemet's membrane in vivo for deep anterior lamellar keratoplasty (DALK), aspects of the present disclosure may be employed to separate other tissue layers for other procedures. For instance, aspects of the present disclosure may be applied to separate tissue layers ex vivo in donor cornea to form a corneal implant.

While the present disclosure has been described with reference to one or more particular embodiments, those skilled in the art will recognize that many changes may be made thereto without departing from the spirit and scope of the present disclosure. Each of these embodiments and obvious variations thereof is contemplated as falling within the spirit and scope of the invention. It is also contemplated that additional embodiments according to aspects of the present disclosure may combine any number of features from any of the embodiments described herein.

We claim:

1. A method for separating tissue in an eye, comprising:
   positioning a body of a separation device on a surface of an eye such that a plurality of needles extending from the body move into tissue of the eye,
   wherein the body of the separation device is configured to receive air from one or more air supplies and comprises one or more air supply channels,
   wherein each needle includes a proximal opening, a distal opening, and a passageway extending between the proximal opening and the distal opening,
   wherein the proximal openings of the needles are coupled to the one or more air supply channels, and
   wherein the distal openings of the needles are spaced from the body of the separation device to be positioned in the tissue of the eye when the body is positioned over the surface of the eye;
   coupling the body of the separation device to one or more air supplies;
   operating the one or more air supplies to deliver air to the one or more air supply channels; and
   creating pressure sufficient to separate tissue in the eye.

2. The method of claim 1, wherein the body of the separation device comprises one or more ports configured to be coupled to the one or more air supplies.

3. The method of claim 1, wherein each air supply comprises a syringe.

4. The method of claim 1, wherein the one or more air supply channels of the body direct the air from the one or more air supplies into the proximal openings, through the passageways, out the distal openings of the needles, and into the tissue of the eye.

5. The method of claim 4, wherein the air directed out of the distal opening of each of the needles has substantially the same airflow.

6. The method of claim 4, wherein the air directed out of the distal opening of one needle has a different airflow than the air directed out of the distal opening of another needle.

7. The method of claim 1, wherein positioning the body of the separation device on the surface of the eye causes the distal openings of the needles to be positioned between the stroma and Descemet's membrane of a cornea of the eye.

8. The method of claim 7, wherein creating pressure sufficient to separate tissue in the eye comprises separating the stroma from Descemet's membrane.

9. The method of claim 1, wherein positioning the body of the separation device on the surface of the eye causes the distal openings of the needles to be positioned approximately 570 μm from the body of the separation device.

10. The method of claim 1, wherein the separation device is coupled to a staging device, the staging device comprising a body that holds the separation device, and wherein the staging device is configured to engage the surface of the eye.

11. The method of claim 10, further comprising coupling the staging device to a vacuum source, the staging device comprising a port coupled to the vacuum source via a connecting tube and one or more vacuum channels connected to the port, and wherein the one or more vacuum channels contain one or more negative pressure openings at the surface of the eye.

12. The method of claim 11, further comprising operating the vacuum source to generate negative pressure in the one or more vacuum channels, wherein the negative pressure in the one or more vacuum channels creates suction at the one or more negative pressure openings, thereby stably positioning the staging device and the separation device on the surface of the eye.

13. The method of claim 12, further comprising operating the vacuum source to release the staging device and the separation device from the surface of the eye.

14. The method of claim 11, wherein the vacuum source comprises a syringe.

15. The method of claim 1, wherein operating the one or more air supplies to deliver air to the one or more air supply channels of the body comprises
   operating a first air supply to deliver a first amount of air to a first set of one or more air supply channels, wherein a first subset of needles receives air from the first air supply via the first set of one or more air supply channels; and
   operating a second air supply to deliver a second amount of air to a second set of one or more air supply channels, wherein a second subset of needles receives air from the second air supply via the second set of one or more air supply channels.

16. The method of claim 15, wherein the air from the first air supply is different in amount than the air from the second air supply.

17. The method of claim 1, wherein the plurality of needles is arranged in a symmetric pattern, a circular pattern, or a grid pattern.

18. The method of claim 1, wherein the plurality of needles is arranged in an asymmetric pattern, a non-circular pattern, or a pattern with non-uniform spacing between the needles.

19. The method of claim 1, further comprising making a cut that extends from the epithelium of the eye to the separated tissue and removing the separated tissue from the eye.

20. The method of claim 1, wherein the eye is a recipient eye or a donor eye.

* * * * *